United States Patent [19]

Ha et al.

[11] Patent Number: 5,180,575
[45] Date of Patent: Jan. 19, 1993

[54] COMPOSITION FOR ENHANCING ORAL HYGIENE, CONTAINING BAMBOO-SALT

[75] Inventors: Jae M. Ha; Kwang L. Jeong; Sung S. Suh, all of Pongmyung-dong, Rep. of Korea

[73] Assignee: Lucky, Ltd., Seoul, Rep. of Korea

[21] Appl. No.: 813,934

[22] Filed: Dec. 27, 1991

[30] Foreign Application Priority Data

Dec. 28, 1990 [KR] Rep. of Korea ............... 90-22099

[51] Int. Cl.⁵ .................. A61K 7/16; A61K 7/26
[52] U.S. Cl. ........................... 404/49; 404/58; 404/680
[58] Field of Search .................. 424/49–58, 424/680

[56] References Cited

U.S. PATENT DOCUMENTS

| | | | |
|---|---|---|---|
| 128,620 | 7/1872 | Hassell | 424/680 |
| 1,466,132 | 8/1923 | Lippert | 424/680 |
| 1,968,858 | 8/1934 | Sheffield et al. | 424/680 |
| 2,658,851 | 11/1953 | Brandenberger et al. | 424/680 |
| 3,689,636 | 9/1972 | Svajda | 424/680 |
| 4,581,226 | 4/1986 | Dillon | 424/680 |
| 4,919,933 | 4/1990 | Park et al. | 424/680 |

Primary Examiner—Shep K. Rose
Attorney, Agent, or Firm—Birch, Stewart, Kolasch & Birch

[57] ABSTRACT

The present invention is directed to an oral hygiene composition which comprises a 0.1 to 30% by weight of a bamboo-salt alone based on the total weight of the composition or a mixture of bamboo-salt and sodium chloride said mixture being in a mixed ratio of 1:5 to 1:15.

10 Claims, No Drawings

COMPOSITION FOR ENHANCING ORAL HYGIENE, CONTAINING BAMBOO-SALT

FIELD OF THE INVENTION

The present invention relates to a composition for enhancing oral hygiene, containing a bamboo-salt alone or in admixture with a sodium chloride. The composition of the present invention can effectively prevent and treat periodontal diseases or prevent teeth from decaying.

BACKGROUND OF THE INVENTION

As is known well, sodium chlorides, antiplasmin agents, allantoin derivatives, vitamines, amino acids and the like, which are used alone or in combination thereof, have been widely used as a composition for enhancing oral hygiene in order to prevent and treat periodontal diseases or to prevent teeth from decaying. However, the preventing and treating effects of periodontal diseases can scarcely be expected. Among the above components, sodium chloride which is known to be effective in preventing and treating the periodontal diseases deteriorates the feeling when the toothpaste is used because the said sodium chloride has its own salty taste and remarkably reduces the foaming properties of the anionic surfactant which is a forming agent to be used in reinforcing the cleaning power in brushing one's teeth.

In order to solve these problems, Japanese Unexamined Patent Publication No. (Sho) 60-92,208 discloses that alkyl sodium sulphates are mixed with N-acylglutamate. Japanese Unexamined Patent Publication No. (Sho) 57-106,606 also discloses that alkyl sodium sulphates and nonionic surfactants such as polyoxyethylene hardened castor oil, polyoxyethylene stearyl alcohol esters, polyoxyethylene stearic acid esters, polyoxyethylene sorbitane monostearates, polyoxyethylene sugar fatty acid esters and the like are used in order to improve the foaming properties of the said surfactants. Further, in Japanese Unexamined Patent Publication No. (sho) 49-13,341, it is attempted to decrease the salty taste by using a flavouring agent comprising of a peppermint oil and a spearmint oil. In addition, in Korean Patent Publication No. 90-6,826, it is attempted to enhance the preventing and treating effects of periodontal diseases by using in admixture with sodium chloride, tranexamic acid, aluminium chlorohydroxy allantoinate and tocopherol acetate, to improve the forming properties by using sodium lauryl sulphate as a foaming agent and polyoxyethylene-polypropylene condensation polymers as a non-ionic surfactant, and to decrease the salty taste by adding a small amount of magnesium chloride. However, no good effects are not obtained.

Under these circumstances, the present inventors have extensively studied in order to solve the above problems. As a result, it has been found that in the course of experiments for evaluating the preventing and treating effects of periodontal diseases and the preventing effect of decayed tooth by using a bamboo-salt which is a nostrum derived from the Korean traditional folk secret recipe, a composition for enhancing oral hygiene, containing a bamboo-salt alone or in admixture with a sodium chloride has an excellent preventing and treating effects and decreases the salty taste of sodium chloride itself, and affords a synergistic effect of the foaming properties.

The bamboo-salts referred herein mean synthetic-processed salts by heating a bamboo and a salt. The bamboo-salt has been known as a nostrum having a greatly enhanced pharmacological effects, which has removed the toxin by repeatedly treating several times the bamboo having a cytogenic function to generate new cells with the salt which functions as a sterilizing agent and an antiseptic in the kiln at a high temperature.

In general, the salts to be used in the preparation of bamboo-salts are bay salts. In addition, common salts, rock salts, reagent grade sodium chlorides and potassium chlorides may be used. As the bamboos, bamboos or black bamboos may be used, but the kind of bamboos is not critical.

The bamboo-salts to be used in the present invention are commercially available. The bamboo-salt are prepared by repeatedly treating several times the bamboo having a cytogenic function to generate new cells with the yellow earth, and the salt which is a sterilizing agent and/or an antiseptic in the kiln at a high temperature (1000° C. or more).

As is known, the bamboos and the salts to be used in the preparation of bamboo-salts have the following efficacy. The bamboos contain cyanine, paeonine, galactose and the like, and have excellent effects (Dongeubogam, Botanical List, Mystic Botanical Roots and Korean Heliochrome Medicinal Herb Pictorial Book). The salts have disinfective and sterilizing effects by virtue of a high osmetic pressure. Moreover, they have effects in the gingival bleeding, edema, inflammation, halitosis and severe periodontal diseases (Dongeubogam, Botanical List, and Mystic Botanical Roots).

As disclosed in the old Chinese Medicinal Books, a process for preparing the bamboo-salts to be used in the present invention is as follows: A large bamboo (triennial bamboo) grown in the sea wind is cut off in the shape that the one side is opened and the other side is closed. The bay salts are hardened by pounding into the bamboo-tube, and then the pine needles, mugworts (collected in Gangwha province) and bamboo leaves are charged thereto in depth of about 1 cm. Then, the yellow earth free of manure collected in the mountain is passed nine times through a fine sieve, dried in the shade, and thereafter thickly kneaded. The bamboo tube is sealed up with the above kneaded yellow earth in depth of about 2 cm from the opened end portion of the bamboo tube.

A large number of bamboo tube filled with the above materials are prepared in the same manner as above. The bamboo tubes thus obtained are heated in the pottery kiln which is made of the yellow earth, at the internal temperature of 1000° C. or more, in which pine trees and pine resins are used as a fuel. After 24 hours, the heated products are taken out of the kiln. At this time, the salt posts absorbed components of bamboos, pine needles, mugworts and yellow earth remain only. Then, the salt posts thus obtained are finely ground, and the ground salts are put into the bamboo tubes in the same manner as above, and then the above heating process is repeated eight times. In the ninth heating process, in order to obtain a high temperature (1500° C. or more), a special stainless furnace installed under ground is used. The above furnace is heated by using pine resins only. The salt products are flowed down like a metallic stain spot by treating with the ninth heating process. After completion of this heating process, the molten salt products are hardened like a stone. The salt masses thus obtained are bamboo-salts, and they are usually used in a pulverized form.

The bamboo-salts are effective in detoxication, life-blood, anti-inflammation, cytogenesis, improvement of habitude, antibiosis, anti-cancer and symptoms of cold [In-Hoon, Kim, Wonder Drug (1986), Synthetic Wonder-Working Remedy, Kwon-Ik, Lee, Wonder-Working Remedy (1989)]. Moreover, the bamboo-salts have been used as folk drugs for 1000 years or more and mainly used by the Buddhist monks.

It has been found that the bamboo-salts thus obtained maintain by far a superior healthy condition of the teethridge with an improvement effect rather than the oral composition comprising of sodium chloride, antiplasmin agent, allantoin, vitamin, amino acid and the like which is used alone or in combination thereof, by measuring the variance of colors in the teethridge. It has also been found that the bamboo-salts have sterilizing effect three times or more than *S. mutans* which is a pathogenic bacteria of the decayed tooth and the general pathogenes in the test of sterilizing power.

SUMMARY OF THE INVENTION

The object of the present invention is to provide a composition for enhancing oral hygiene, containing a bamboo-salt alone or in admixture with sodium chloride.

Another object of the present invention is to provide a method of preventing and treating periodontal diseases or preventing teeth from decaying.

Further objects and advantages of this invention will be apparent from the following descriptions.

DETAILED DESCRIPTION OF THE INVENTION

The present invention provides a composition for enhancing oral hygiene by adding a bamboo-salt or a mixture of bamboo-salt and sodium chloride to the components which are conventionally used in the tooth paste, mouth detergent, artificial teeth cleanser, chewing gum, massage cream for teethridge and the like.

The major components of a bamboo-salt according to the present invention are sodium, chlorine, iron, calcium, magnesium, manganese, phosphorus, zinc, sulfur and the like.

The amount of a bamboo-salt or a mixture of bamboo-salt and sodium chloride is 0.1 to 30% by weight, preferably 1 to 15% by weight to the total weight of the components which are conventionally necessary for preparing mouth preparations, and a composition for enhancing oral hygiene. When the mixture of bamboo-salt and sodium chloride is used, the mixed ratio of bamboo-salt to sodium chloride is preferably 1/5 to 1/15.

When the amount of bamboo-salt or its mixture is less than 0.1% by weight, the preventing and treating effects of periodontal diseases as well as the preventing effect of decayed tooth may not be expected. On the other hand, when the amount of bamboo-salt or its mixture exceeds 30% by weight, the users have an unpleasant feeling due to the existence of the inherent salty taste of bamboo-salt and/or sodium chloride and an unpleasant odor of sulphide existing in the bamboo-salt. Furthermore, by reducing the foaming properties of the surfactant, a feeling of use may be deteriorated.

The amounts of other components of the present invention may be properly adjusted depending on the kind of oral composition and the object of use.

As an example, a toothpaste composition includes conventional tooth paste components, for example, polishing agents such as dicalcium phosphate, silicon dioxide aluminum hydroxide, calcium carbonate and the like; humectants such as sorbitol, glycerin, polyethylene glycol and the like; foaming agents such as sodium alkylsulphate, polyoxyethylene-polyoxypropylene condensation polymer and the like; sweetening agents such as saccharin, aspartame and the like; flavouring agents such as peppermint oil, spearmint oil and the like; preservatives such as methyl paraoxy benzoic acid and the like; therapeutic agents such as sodium fluoride, chlorhexidine, tranexamic acid, allantoin and the like; and the binders. The toothpaste composition may be prepared by adding 0.1-30% by weight of a bamboo-salt or a mixture of bamboo-salt and sodium chloride to the above conventional toothpaste components in a known manner in the art of toothpastes.

As an embodiment of the present invention, the oral composition is prepared by mixing a proper amount of conventional components to be used in the mouth preparations with a bamboo-salt alone or a mixture of bamboo-salt and sodium chloride which is effective in preventing and treating periodontal diseases or preventing teeth from decaying at an amount of 0.1-30% by weight, preferably 1-15% by weight.

Among the compositions for enhancing oral hygiene, a toothpaste composition is prepared as follows: Firstly, a small amount of sodium carboxymethyl cellulose, saccharin and preservative in the form of powder is dispersed in the non-crystalline sorbitol solution, diluted with the distilled water, and blended in the mixer. Then, a polishing agent (dicalcium phosphate, etc.), sodium chloride and bamboo-salt are added thereto, and then blended. Finally, a foaming agent(sodium alkylsulphate), preservative and flavouring agent are added to the resulting blend, and then blended under vacuum to obtain a toothpaste composition.

Other oral hygiene compositions may be prepared in the conventional manner.

The present invention is further illustrated by the following Examples and Comparative Examples.

In the following Examples and Comparative Examples, all the percents are by weight unless otherwise stated.

EXAMPLES 1 TO 2 AND COMPARATIVE EXAMPLES 1 TO 4

The toothpaste compositions were prepared by using the components as shown in Table 1.

TABLE 1

| Components | Example Nos. | | Comparative Example Nos. | | | |
| --- | --- | --- | --- | --- | --- | --- |
| | 1 (%) | 2 (%) | 1 (%) | 2 (%) | 3 (%) | 4 (%) |
| Dicalcium phosphate | 40.0 | 40.0 | 40.0 | 40.0 | 40.0 | 40.0 |
| Non-crystalline sorbitol solution | 25.0 | 25.0 | 25.0 | 25.0 | 25.0 | 25.0 |
| Bamboo-salt | 2.0 | 5.0 | — | — | — | — |
| Sodium chloride | — | — | 10 | 15 | 20 | — |
| Aluminum chlorohydroxy allantoinate | — | — | 0.1 | 0.1 | 0.1 | — |
| Tocopherol acetate | — | — | 0.1 | 0.1 | 0.1 | — |
| Tranexamic acid | — | — | 0.1 | 0.1 | 0.1 | — |
| l-sodium glutamate | — | — | 0.01 | 0.01 | 0.01 | — |
| Sodium alkylsulphate | 2.0 | 2.0 | 2.0 | 2.0 | 2.0 | 2.0 |
| Sodium saccharin | 0.1 | 0.1 | 0.1 | 0.1 | 0.1 | 0.1 |
| Sodium carboxymethyl cellulose | 1.0 | 1.0 | 1.0 | 1.0 | 1.0 | 1.0 |
| Flavouring agent | 0.8 | 0.8 | 0.8 | 0.8 | 0.8 | 0.8 |
| By adding distilled water, up to | 100 | 100 | 100 | 100 | 100 | 100 |

TABLE 1-continued

| Components | Example Nos. 1 (%) | Example Nos. 2 (%) | Comparative Example Nos. 1 (%) | Comparative Example Nos. 2 (%) | Comparative Example Nos. 3 (%) | Comparative Example Nos. 4 (%) |
|---|---|---|---|---|---|---|
| U.V Spectrophotometer, transmittance (%) | 70 | 90 | 10 | 10 | 20 | 0 |

EXAMPLES 3 TO 6

The toothpaste compositions were prepared by using the components as shown in Table 2.

COMPARATIVE EXAMPLES 5 TO 8

The conventional toothpaste compositions were prepared by using the components as shown in Table 2.

TABLE 2

| Components | Example Nos. 3 (%) | Example Nos. 4 (%) | Example Nos. 5 (%) | Example Nos. 6 (%) | Comparative Example Nos. 5 (%) | Comparative Example Nos. 6 (%) | Comparative Example Nos. 7 (%) | Comparative Example Nos. 8 (%) |
|---|---|---|---|---|---|---|---|---|
| Dicalcium phosphate | 35.0 | 35.0 | 35.0 | 23.0 | 35.0 | 25.0 | 40.0 | — |
| Calcium carbonate | — | — | — | — | — | — | — | 35.0 |
| Precipitated silica | — | — | — | — | — | — | 2.0 | — |
| Anhydrous silicic acid | — | — | — | — | — | — | — | 1.5 |
| Non-crystalline sorbitol solution | 35.0 | 35.0 | 35.0 | 23.0 | 35.0 | 35.0 | 30.0 | — |
| Sorbitol solution | — | — | — | — | — | — | — | 7.0 |
| Glycerin | — | — | — | — | — | — | — | 13.0 |
| Sodium chloride | 10.0 | — | — | — | — | — | 15.0 | 20.0 |
| Bamboo-salt | 0.5 | 5.0 | 10.0 | 30.0 | 0.05 | 35.0 | — | — |
| Tranexamic acid | 0.05 | 0.05 | 0.05 | 0.05 | 0.05 | 0.05 | 0.05 | 0.05 |
| Aluminum chlorohydroxy allantoinate | 0.1 | 0.1 | 0.1 | 0.1 | 0.1 | 0.1 | 0.1 | 0.1 |
| Tocopherol acetate | 0.1 | 0.1 | 0.1 | 0.1 | 0.1 | 0.1 | 0.1 | 0.1 |
| E-amino caproic arid | 0.05 | 0.05 | 0.05 | 0.05 | 0.05 | 0.05 | 0.05 | 0.05 |
| Sodium alkylsulphate | 2.0 | 2.0 | 2.0 | 2.0 | 2.0 | 2.0 | 2.0 | 2.0 |
| Sugar-fatty acid ester | — | — | — | — | — | — | — | 2.5 |
| N-acyl glutamate | — | — | — | — | 2.0 | — | — | — |
| Magnesium chloride | 0.05 | 0.05 | 0.1 | 0.1 | 0.05 | 0.1 | 0.1 | 0.1 |
| Trimagnesium phosphate | 0.05 | 0.05 | 0.05 | 0.05 | 0.05 | 0.05 | 0.05 | 0.05 |
| Sodium saccharin | 0.1 | 0.1 | 0.1 | 0.1 | 0.1 | 0.1 | 0.1 | 0.1 |
| Methyl Paraben | 0.05 | 0.05 | 0.05 | 0.05 | 0.15 | 0.05 | 0.15 | 0.15 |
| Sodium carboxymethyl cellulose | 0.8 | 0.8 | 0.8 | 0.6 | 1.0 | 0.5 | 1.0 | 1.0 |
| Flavouring agent | 0.1 | 0.1 | 0.1 | 0.1 | 0.1 | 0.1 | 0.1 | 0.1 |
| By adding distilled water, up to | 100.0 | 100.0 | 100.0 | 100.0 | 100.0 | 100.0 | 100.0 | 100.0 |

EXPERIMENTAL EXAMPLE 1

Bactericidal Test on ToothPastes of Examples 1 to 2 and Comparative Examples 1 to 4

Each toothpaste sample prepared by using the components as shown in the above Table 1 was taken with 10% by weight based on the total weight of the compositions. The bactericidal test on the aerobic and anaerobic bacteria was carried out by a conventional method. After each toothpaste sample being standed at 37° C. for 24 hours, the growing condition of bacteria was observed by using an U.V. spectrophotometer, and each transmittance observed was shown in Table 1. The measurement of transmittance was carried out by using a Perkin-Elmer Lamda 15 UV/VIS spectrophotometer. The evaluation of bactericidal effects was carried out in Examples 1 to 2 and Comparative Examples 1 to 3 on the basis of Comparative Example 4 on the condition that the transmittance of a toothpaste prepared in the Comparative Example 4 is zero.

EXPERIMENTAL EXAMPLE 2

Preventing Effect of Periodontal Diseases and Comparative Experiments of Toothpastes of Examples 3 to 6 and Comparative Examples 5 to 8

The teeth were brushed for three minutes by using the toothpastes according to the present invention and the toothpastes obtained in the Comparative Examples, respectively, for 20 days (3 times per one day). Thereafter, the healthy condition of the teethridge and the improvement effects thereof were tested by measuring the variance of colors in the teethridge. The measurement of the variance of colors was carried out by using a Japanese Whole Color Σ80 Colorimeter. The results are set forth in Tables 3 and 4.

TABLE 3

| Kind of toothpaste | User | Pre-Use L | Pre-Use a | Pre-Use b | Post-Use L | Post-Use a | Post-Use b |
|---|---|---|---|---|---|---|---|
| Example 3 | a | 60.6 | 18.5 | 4.0 | 65.8 | 23.4 | 4.8 |
|  | b | 64.2 | 21.3 | 2.4 | 69.1 | 25.3 | 3.8 |
| Example 4 | c | 62.4 | 18.2 | 2.8 | 69.5 | 25.0 | 4.0 |
|  | d | 65.0 | 19.0 | 1.4 | 70.2 | 24.2 | 2.2 |
| Example 5 | e | 60.5 | 16.4 | 5.0 | 67.8 | 29.1 | 5.5 |
|  | f | 63.2 | 18.9 | 3.8 | 71.2 | 26.6 | 5.0 |
| Example 6 | g | 62.5 | 19.2 | 3.5 | 71.3 | 25.4 | 4.4 |
|  | h | 66.7 | 22.4 | 0.5 | 75.0 | 28.6 | 1.2 |
| Comparative Example 5 | i | 64.3 | 25.1 | 2.4 | 66.2 | 26.3 | 5.0 |
|  | j | 60.7 | 21.5 | 3.8 | 63.5 | 23.1 | 6.2 |
| Comparative Example 6 | k | 63.2 | 20.8 | 5.1 | 72.1 | 30.3 | 6.0 |
|  | l | 60.2 | 24.1 | 3.6 | 69.8 | 28.4 | 4.8 |
| Comparative Example 7 | m | 60.3 | 17.2 | 2.5 | 64.1 | 22.4 | 5.5 |
|  | n | 64.1 | 18.5 | 1.1 | 68.0 | 23.8 | 3.5 |
| Comparative Example 8 | o | 62.8 | 16.5 | 0.8 | 66.9 | 19.3 | 2.9 |
|  | p | 64.2 | 20.4 | 3.4 | 68.6 | 23.0 | 5.6 |

TABLE 4

| Kind of toothpaste | Average Variance Value L | Average Variance Value a | Average Variance Value b |
|---|---|---|---|
| Example 3 | 4.8 | 4.5 | 1.2 |
| Example 4 | 6.2 | 6.0 | 1.0 |
| Example 5 | 7.7 | 10.2 | 0.8 |
| Example 6 | 8.6 | 6.2 | 0.8 |
| Comparative Example 5 | 2.4 | 1.4 | 2.5 |
| Comparative Example 6 | 9.25 | 5.9 | 1.05 |
| Comparative Example 7 | 3.9 | 5.3 | 2.7 |

TABLE 4-continued

| Kind of toothpaste | Average Variance Value | | |
|---|---|---|---|
| | L | a | b |
| Comparative Example 8 | 4.3 | 2.7 | 2.2 |

Notes:
L: Lightness index
a: (+) Degree of red color, (−) Degree of green color
b: (+) Degree of yellow color, (−) Degree of blue color As can be seen from the above Tables 3 and 4, the teethridge is more healthy, the lightness index and a degree of red color are more higher, and a degree of yellow color is more lower. thus, a clear pink color appears.

EXPERIMENTAL RESULTS

As the toothpastes according to the Examples appear a more clean pink color than the one of the toothpastes according to the Comparative Examples, it is apparent that the toothpastes according to the present invention are more effective than the conventional toothpastes in preventing and treating the periodontal diseases and in enhancing the health of teethridge. As shown in the Comparative Example 5, a tooth paste having a bamboo-salt(less than 0.1% by weight) showed a low effect. On the contrary, in the Comparative Example 6, the effect was good, but the feeling of use was too bad due to the existence of the odor of sulphide and the salty taste of a bamboo-salt.

EXAMPLE 7

Mouth Detergent

| | |
|---|---|
| Ethanol (90%) | 20.0% |
| Glycerine (98%) | 10.0% |
| Polyoxyethylene-polyoxypropylene copolymer | 1.0% |
| Aluminum chlorohydroxy allantoinate | 0.1% |
| Tranexamic acid | 0.05% |
| Bamboo-salt | 2% |
| Sodium saccharin | 0.1% |
| Flavouring agent | 1.0% |
| By adding distilled water, up to | 100.0% |

EXAMPLE 8

Artificial Teeth Cleanser

| | |
|---|---|
| Sodium bicarbonate | 30.0% |
| Stannic acid | 27.0% |
| Sodium sarcosinate-cocoanut oil | 5.0% |
| Sodium lauryl sulfate | 5.0% |
| Benzalkonium chloride | 2.0% |
| EDTA | 5.0% |
| Sodium tripolyposphate | 14.0% |
| Polyethylene glycol | 2.0% |
| Bamboo-salt | 5.0% |
| Flavouring agent | q.s. |

EXAMPLE 9

Chewing Gum

| | |
|---|---|
| Gum base | 25.0% |
| Sorbitol | 44.0% |
| Mannitol | 12.0% |
| Glycerine | 13.0% |
| Lecithin | 0.5% |
| Sweetening agent | 2.0% |
| Bamboo-salt | 2.0% |
| Flavouring agent | 1.5% |

EXAMPLE 10

Massage Cream For Teethridge

| | |
|---|---|
| Glycerol monolaurate | 3.0% |
| Oleic alcoholate | 5.0% |
| Polyethylene glycol | 15.0% |
| White Vaseline | 3.0% |
| Monosodium N-palmitic glutamate | 0.5% |
| Hydroxyethyl cellulose | 5.0% |
| Tocopherol acetate | 0.1% |
| Bamboo-salt | 3.0% |
| Sweetening agent | 0.2% |
| Aluminum chlorohydroxy allantoinate | 3.0% |
| Flavouring agent | 0.3% |
| By adding distilled water, up to | 100.0% |

All the compositions of Examples 3 to 10 showed an excellent preventing and treating effects for periodontal diseases and an inhibiting effect for decayed tooth.

What is claimed is:

1. An oral hygiene composition which comprises a 0.1 to 30% by weight of a bamboo-salt alone based on the total weight of the composition or a mixture of bamboo-salt and sodium chloride said mixture being in a mixed ratio of 1:5 to 1:15.
2. The composition according to claim 1, characterized in that the composition contains 1 to 15% by weight of a bamboo-salt alone or a mixture of bamboo-salt and sodium chloride based on the total weight of the composition.
3. The composition according to claims 1 or 2, characterized in that the composition is a toothpaste.
4. The composition according to claims 1 or 2, characterized in that the composition is a mouth detergent.
5. The composition according to claims 1 or 2, characterized in that the composition is an artificial teeth cleanser.
6. The composition according to claims 1 or 2, characterized in that the composition is a chewing gum.
7. The composition according to claims 1 or 2, characterized in that the composition is a massage cream for teethridge.
8. The composition according to claim 3, characterized in that the composition contains polishing agents, wetting agents, foaming agents sweetening agents, flavouring agents, preservatives, pharmacologically active ingredients and binders.
9. The composition according to claims 1 or 2, characterized in that the composition contains a bamboo-salt alone.
10. The composition according to claims 1 or 2, characterized in that the composition contains a mixture of bamboo-salt and sodium chloride.

* * * * *